(12) United States Patent
Brenc et al.

(10) Patent No.: US 12,091,648 B2
(45) Date of Patent: *Sep. 17, 2024

(54) SYSTEM AND METHOD FOR GENERATING BUBBLES IN A VESSEL

(71) Applicant: LanzaTech, Inc., Skokie, IL (US)

(72) Inventors: Rachel Jane Brenc, Elmhurst, IL (US); Robert John Conrado, Washington, DC (US); Joss Anton Coombes, Chicago, IL (US); Elham Ebrahimiaqda, Minneapolis, MN (US); Allan Haiming Gao, West Chester, PA (US); Brian Nelson Horton, Vidalia, GA (US); Xueliang Li, Morton Grove, IL (US); Mayur Sathe, Skokie, IL (US); Curtis Paul Studebaker, Edmonton (CA)

(73) Assignee: LanzaTech, Inc., Skokie, IL (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/453,476

(22) Filed: Nov. 3, 2021

(65) Prior Publication Data

US 2023/0132925 A1    May 4, 2023

(51) Int. Cl.
*C10G 2/00*       (2006.01)
*B01F 23/231*    (2022.01)
*B01J 8/22*        (2006.01)
*C12M 1/00*      (2006.01)
*C12P 7/06*       (2006.01)
*B01F 101/44*    (2022.01)

(52) U.S. Cl.
CPC ....... *C12M 21/12* (2013.01); *B01F 23/23123* (2022.01); *C12P 7/06* (2013.01); *B01F 23/23112* (2022.01); *B01F 23/231231* (2022.01); *B01F 2101/44* (2022.01); *B01F 2215/0431* (2013.01); *B01F 2215/0481* (2013.01)

(58) Field of Classification Search
CPC ................. B01J 8/22; B01J 2208/0058; B01J 2208/00911; B01J 2208/00743; B01J 2208/00761; C10G 2/34
See application file for complete search history.

(56) References Cited

U.S. PATENT DOCUMENTS

| 2,657,174 A | 10/1953 | Stich |
| 3,220,706 A | 11/1965 | Valdespino |
| 4,043,771 A | 8/1977 | Anand |
| 4,336,224 A | 6/1982 | Siposs |
| 4,415,341 A | 11/1983 | Echtler |
| 4,938,865 A | 7/1990 | Jameson |
| 5,173,429 A | 12/1992 | Gaddy et al. |
| 5,593,886 A | 1/1997 | Gaddy |
| 5,951,875 A | 9/1999 | Kanel et al. |
| 6,358,483 B1 | 3/2002 | Trott |
| 6,368,819 B1 | 4/2002 | Gaddy et al. |
| 7,972,824 B2 | 7/2011 | Simpson |
| 8,143,037 B2 | 3/2012 | Zahn et al. |
| 8,251,228 B2 | 8/2012 | Clayton |
| 8,293,509 B2 | 10/2012 | Simpson |
| 8,658,408 B2 | 2/2014 | Simpson |
| 8,900,836 B2 | 12/2014 | Simpson |
| 9,068,202 B2 | 6/2015 | Tran |
| 9,284,564 B2 | 3/2016 | Mueller |
| 9,327,251 B2 | 5/2016 | Li |
| 9,347,076 B2 | 5/2016 | Liew |
| 9,359,611 B2 | 6/2016 | Koepke |
| 9,410,130 B2 | 8/2016 | Koepke |
| 9,593,598 B2 | 3/2017 | Bapat |
| 9,738,875 B2 | 8/2017 | Koepke |
| 9,890,384 B2 | 2/2018 | Mueller |
| 9,994,878 B2 | 6/2018 | Koepke |
| 10,174,303 B2 | 1/2019 | Behrendorff |
| 10,590,406 B2 | 3/2020 | Koepke |
| 10,913,958 B2 | 2/2021 | Koepke |
| 2006/0116531 A1* | 6/2006 | Wonders ............... C07C 51/265 702/22 |
| 2007/0254965 A1 | 11/2007 | Boer |
| 2009/0035848 A1 | 2/2009 | Hickey |
| 2010/0002534 A1 | 1/2010 | Zimmerman |
| 2010/0080743 A1 | 4/2010 | Cocco |
| 2010/0193408 A1 | 8/2010 | Jameson |
| 2012/0045807 A1 | 2/2012 | Simpson |
| 2013/0157322 A1 | 6/2013 | Simpson |

(Continued)

FOREIGN PATENT DOCUMENTS

AU    677542 B2    4/1997
CN    1241149 A    1/2000
(Continued)

OTHER PUBLICATIONS

Lalitha Chockalingam, Mutharasu, "Multiphase Flow Modeling for Design and Optimization of a Novel Down-flow Bubble Column" (2017). LSU Doctoral Dissertations. 4181.
Kalaga, Dinesh V., et al. "Scale-up of a downflow bubble column: Experimental investigations." Chemical Engineering Journal (2020).
International Search Report issued in corresponding International Application No. PCT/NZ2014/00009) dated Aug. 7, 2014, 4 pages.
Abrini, J. Naveau, H. & Nyns, E.J., Archives of Microbiology, (1994), 161, 345-351.
Bredwell et al., Mass Transfer Properties of Microbubbles, Part 1: Experimental Studies, Biotechnol. Prog., (1998), 14, 31-38.
Kopke, Michael et al., 2,3 butanediol production by acetogenic bacteria, an alternative route to chemical synthesis, using industrial waste gas, Appln. Environ. Microbiol., 17, Jun. 2011, vol. 77, No. 15, pp. 5467-5475.

(Continued)

*Primary Examiner* — Maryam Monshipouri

(57) ABSTRACT

The systems and methods disclosed herein provide for the efficient generation of fine bubbles. In particular, systems and methods for use in bioreactors are disclosed herein providing a superior means to produce useful fermentation products by the biological fermentation of fine bubble waste substrates injected into a liquid broth containing a microorganism culture.

10 Claims, 8 Drawing Sheets

(56) References Cited

U.S. PATENT DOCUMENTS

| | | |
|---|---|---|
| 2014/0212937 A1 | 7/2014 | Li |
| 2019/0185888 A1 | 6/2019 | Koepke |
| 2021/0292732 A1 | 9/2021 | Liew |

FOREIGN PATENT DOCUMENTS

| | | |
|---|---|---|
| GB | 2504505 A | 2/2014 |
| JP | 2010247132 A | 11/2010 |
| KR | 100802204 B1 | 2/2008 |
| KR | 20190013145 A | 2/2019 |
| WO | 2002008438 A2 | 1/2002 |
| WO | 2004018067 A2 | 3/2004 |
| WO | 2008028055 A2 | 3/2008 |
| WO | 2008115080 A1 | 9/2008 |
| WO | 2009064200 A2 | 5/2009 |
| WO | 2011129775 A1 | 10/2011 |

OTHER PUBLICATIONS

Tanner, R.S. Miller, L.M., & Yang, D., International Journal of Systematic Bacteriology, (1993), 43, 232-236.

Terasaka et al., Chemical Engineering Science, 2011, vol. 66, p. 3172-3179.

Tirado-Acevedo O., Production of Bioethanol from Synthesis Gas Using Clostridium ljungdahlii. PhD thesis, North Carolina State University, 2010.

Tyurin, M. & Kiriukhin, M., Electrofusion of cells of Acetogen *Clostridium* sp. MT 351 with erm(B) or cat in the chromosome, Journal of Biotech Research, (2012), 4:1-12.1-12.

International Search Report and Written Opinion issued in International Application No. PCT/US2022/078967, mailed Feb. 28, 2023, 10 pages.

International Search Report and Written Opinion issued in International Application No. PCT/US2022/078973, mailed Feb. 27, 2023, 9 pages.

Ong, B.C. et al., "Computed Tomographic Investigation of the Influence of Gas Sparger Design on Gas Holdup Distribution in a Bubble Column", Ind. Eng. Chem. Res., 2009, vol. 48, pp. 58-68.

Kracht et al., "Controlling bubble size using a frit and sleeve sparger," Minerals Engineering, vol. 21, Issue 9, Aug. 2008, pp. 660-663.

Smith et al. "Bubble Column Reactors for Wastewater Treatment. 2. The Effect of Sparger Design on Sublation Column Hydrodynamics in the Homogeneous Flow Regime," Ind. Eng. Chem. Res. 1996, 35, 5, 1700-1710.

\* cited by examiner

SYSTEM AND METHOD FOR GENERATING BUBBLES IN A VESSEL

FIELD

Embodiments described herein generally relate to systems for the generation of fine bubbles. Other embodiments described herein generally related to methods for injecting gas bubbles into a liquid and subsequently generating fine bubbles. In particular, systems and methods for use in reactors, such as bioreactors, are disclosed herein and are generally related to the efficient production of useful fermentation products by the efficient biological fermentation of waste substrates injected into a liquid broth containing a microorganism culture.

BACKGROUND

A sparger is a device that injects gas into a liquid. Gas injected into the liquid from a sparger forms bubbles in the liquid. In particular, the sparger design and arrangement dictates the bubble size, bubble distribution, and related pattern of gas injection across a cross-section of a reaction vessel. Various processes use the injected gas bubbles in chemical or biological reactions to produce a final product. Previous systems and methods use various sparger designs and configurations to inject gas bubbles into a liquid, but such systems and methods are limited in the overall superficial gas and liquid velocities required to reduce overall reaction system component size and space requirements, and to maximize the quantities of final product generated by conventional systems and methods.

Biological reactions and related reaction systems may employ spargers to inject gas bubbles into a liquid reaction media or fermentation broth to convert waste products, such as CO, or $CO_2$ and $H_2$, or $CH_4$, or mixtures thereof into useful products such as ethanol ($C_2H_5OH$) through microbial fermentation. Gaseous waste products are introduced into the liquid reaction media or fermentation broth by sparging. The gaseous waste products in the form of gas bubbles are used by the microbes in the fermentation broth as carbon and possibly energy sources resulting in the generation of at least one useful product. The concentration of the gas bubbles in the fermentation broth, the amount of time microbes have to process the gas bubbles in the fermentation broth, and the superficial surface area of the bubbles in the fermentation broth may significantly impact the overall productivity of microbial fermentation and generation of useful products. Unfortunately, waste gases, such as CO, $CO_2$, and $CH_4$, are known to have poor solubility characteristics thus limiting the quantities of substrate gas soluble in the fermentation broth and available for processing by the microbes and limiting the amount of useful product generated.

Maximizing the amount of desired product generated in chemical or biological reactions using spargers to inject a gas substrate into a reaction liquid may also be achieved by increasing the gas bubble superficial surface area. Reduction of bubble size and/or generating fine bubbles increases the superficial surface area of the bubbles. The greater superficial surface area of fine bubbles results in a greater gas to liquid mass transfer ultimately increasing the amount of contact of microbes with the substrate in order for the microbe to convert the substrate into a desired product. An example of systems and methods used to create microbubbles include those described in U.S. Pat. No. 9,327,251, incorporated herein by reference in its entirety for all purposes.

Another potential means to enhance the efficiency and to maximize products generated in chemical or biological reactions using spargers may be achieved by increasing the overall superficial gas and liquid velocities used to break bubbles into fine bubbles in a reactor system operating with downward fluid flow. By increasing the overall superficial gas and liquid velocities, injected sparger bubbles can be broken into fine bubbles that flow downward with the fluid flow in the vessel. As compared to upward flow systems, the downward flow of fluid extends the time during which the microbes contact the substrate-filled fine bubbles and generate product as a result of increased bubble residence time. By establishing a system with increased superficial gas and liquid velocities, the overall size of a reaction vessel may be reduced resulting in a decrease in the overall footprint and capital costs of such systems.

Previous systems failed to create optimal-sized fine bubbles for use in chemical and biological reactions. As such, the generation of useful products from these reactions is suboptimal. Previous systems and methods also failed to achieve overall superficial gas and liquid velocities to efficiently produce commercially valuable chemical and biological reaction products. Previous systems have been unable to exceed superficial velocities of the gas phase of about 25 mm/s. See e.g., Kalaga, Dinesh V., Ansari, Manizheh, Turney, Damon E., Hernandez-Alvarado, Freddy, Kleinbart, Simon, ArunKumar, K. E., Joshi, Jyeshtharaj B., Banerjee, Sanjoy, & Kawaji, Masahiro. *Scale-up of a downflow bubble column: Experimental investigations*. Further, previous systems failed to provide high mass transfer coefficients required to design more efficient and smaller systems. Such limitations of the previous systems lead to increased space requirements due to the larger system components needed to generate useful quantities of reaction products. Accordingly, there remains a need for a system and method that enables the creation of optimal sized fine bubbles, increased gas to liquid mass transfer capabilities, and required superficial gas and liquid velocities for efficiently producing desired chemical and biological reaction products while reducing the overall system footprint and costs. The systems and methods disclosed herein overcome the disadvantages and limitations of previous and known conventional systems.

SUMMARY

The following presents a simplified summary of various embodiments described herein. This summary is not an extensive overview and is not intended to identify key or critical elements or to delineate the scope of the claims. The following summary merely presents some concepts in a simplified form as an introductory prelude to the more detailed description provided below.

To overcome limitations of previous systems and methods described above, and to overcome other limitations that will be apparent upon reading and understanding the present specification, embodiments described herein are directed to systems and methods for the efficient generation of fine bubbles.

In one embodiment, the systems disclosed herein relate to generating fine bubbles and may include a vessel containing a liquid, a plate comprising a plurality of orifices positioned in an upper portion of the vessel and configured to accelerate at least a portion of the liquid in the vessel, and at least one sparger positioned within the vessel with a surface of the sparger positioned from about 50 mm to about 300 mm, 500 mm, or 1000 mm from a bottom of the plate. The sparger may be configured to inject bubbles into the liquid. In some examples, the sparger may be positioned within the vessel to create a first zone for the bubbles to rise within the vessel, and to create a second zone for the accelerated liquid to break the bubbles into fine bubbles and for fluid to flow through the vessel. The fluid may include the accelerated portion of the liquid and fine bubbles. In still other examples, the superficial velocity of the gas phase in the vessel may be at least 30 mm/s. The sparger may be a sintered sparger or an orifice sparger. The thickness of the plate may be about 1 mm to about 25 mm. The accelerated liquid may have a velocity of about 8000 mm/s to about 17000 mm/s. In other examples, the accelerated liquid may have a velocity of about 12000 mm/s to about 17000 mm/s. In some examples, the bubbles injected into the liquid from the sparger may have a diameter of about 2 mm to about 20 mm. In another example, the bubbles injected into the liquid from the sparger may have a diameter of about 5 mm to about 15 mm, or from about 7 mm to about 13 mm. The fine bubbles may have a diameter of about 0.1 mm to about 5 mm, or about 0.2 mm to about 1.5 mm. The plurality of orifices may also be configured to accelerate at least 90% of the liquid in the vessel.

In another embodiment, the methods disclosed herein relate to generating fine bubbles that may include sparging gas into a vessel containing a liquid via at least one sparger positioned within the vessel and configured to inject bubbles into the liquid and accelerating a portion of the liquid in the vessel via a perforated plate positioned in an upper portion of the vessel, in which the liquid may be accelerated from the plate to break the bubbles into fine bubbles. In some examples, a superficial velocity of the gas phase in the vessel may be at least 30 mm/s. In other examples, the superficial velocity of the gas phase in the vessel may be from about 30 mm/s to about 80 mm/s. The sparger may be a sintered sparger or an orifice sparger. The liquid may be accelerated from the perforated plate at a velocity of about 8000 mm/s to about 17000 mm/s. In some examples, the liquid may be accelerated from the perforated plate at a velocity of about 12000 mm/s to about 17000 mm/s. The bubbles injected into the liquid from the sparger may have a diameter of about 2 mm to about 20 mm, or from greater than 5 mm to about 15 mm, or from about 7 mm to about 13 mm. Often the bubbles injected into the liquid from the sparger are not spherical. The injected bubbles may be referred to as coarse bubbles. In contrast, the fine bubbles may have a diameter of about 0.1 mm to about 5 mm, or about 0.2 mm to about 1.5 mm. The fine bubbles are typically spherical. The liquid stream may be introduced at a location proximate to the plate. The sparger may be positioned perpendicular or parallel to the plate, and a top or side surface of the sparger may be positioned from about 50 mm to about 300 mm, 500 mm, or 1000 mm from a bottom of the plate.

In yet another embodiment, the systems disclosed herein relate to a bioreactor that may include a vessel containing a liquid growth medium, a plate that may include a plurality of orifices positioned in an upper portion of the vessel and configured to accelerate at least a portion of the liquid growth medium in the vessel, a substrate that may include at least one C1 carbon source, at least one sparger positioned within the vessel with a surface of the sparger that may be positioned from about 50 mm to about 300 mm, 500 mm, or 1000 mm from a bottom of the plate and the sparger configured to inject substrate bubbles into the liquid growth medium. The sparger positioned within the vessel may create a first zone for the substrate bubbles to rise within the vessel, and a second zone for the accelerated liquid growth medium to break the substrate bubbles into substrate fine bubbles, and for fluid to flow through the vessel. The fluid may have the accelerated portion of the liquid growth medium and may have the substrate fine bubbles, and a culture of at least one microorganism in the liquid growth medium. The culture of at least one microorganism may anaerobically ferment the substrate to produce at least one fermentation product.

In still another embodiment, the methods disclosed herein relate to generating substrate fine bubbles in a bioreactor and may include sparging substrate bubbles of at least one C1 carbon source into a vessel containing a liquid growth medium via at least one sparger positioned within the vessel and accelerating a portion of the liquid growth medium in the vessel via a perforated plate positioned in an upper portion of the vessel. The liquid growth medium accelerated from the plate may break the substrate bubbles into substrate fine bubbles. A superficial velocity of the gas phase in the vessel may be at least 30 mm/s. A culture of at least one microorganism may be included in the liquid growth medium and may anaerobically ferment the substrate to produce at least one fermentation product.

These features, along with many others, are discussed in greater detail below.

BRIEF DESCRIPTION OF THE DRAWINGS

A more complete understanding of embodiments described herein, and the advantages thereof may be acquired by referring to the following description in consideration of the accompanying drawings, in which like reference numbers indicate like features, and wherein.

DETAILED DESCRIPTION

Figure 1:
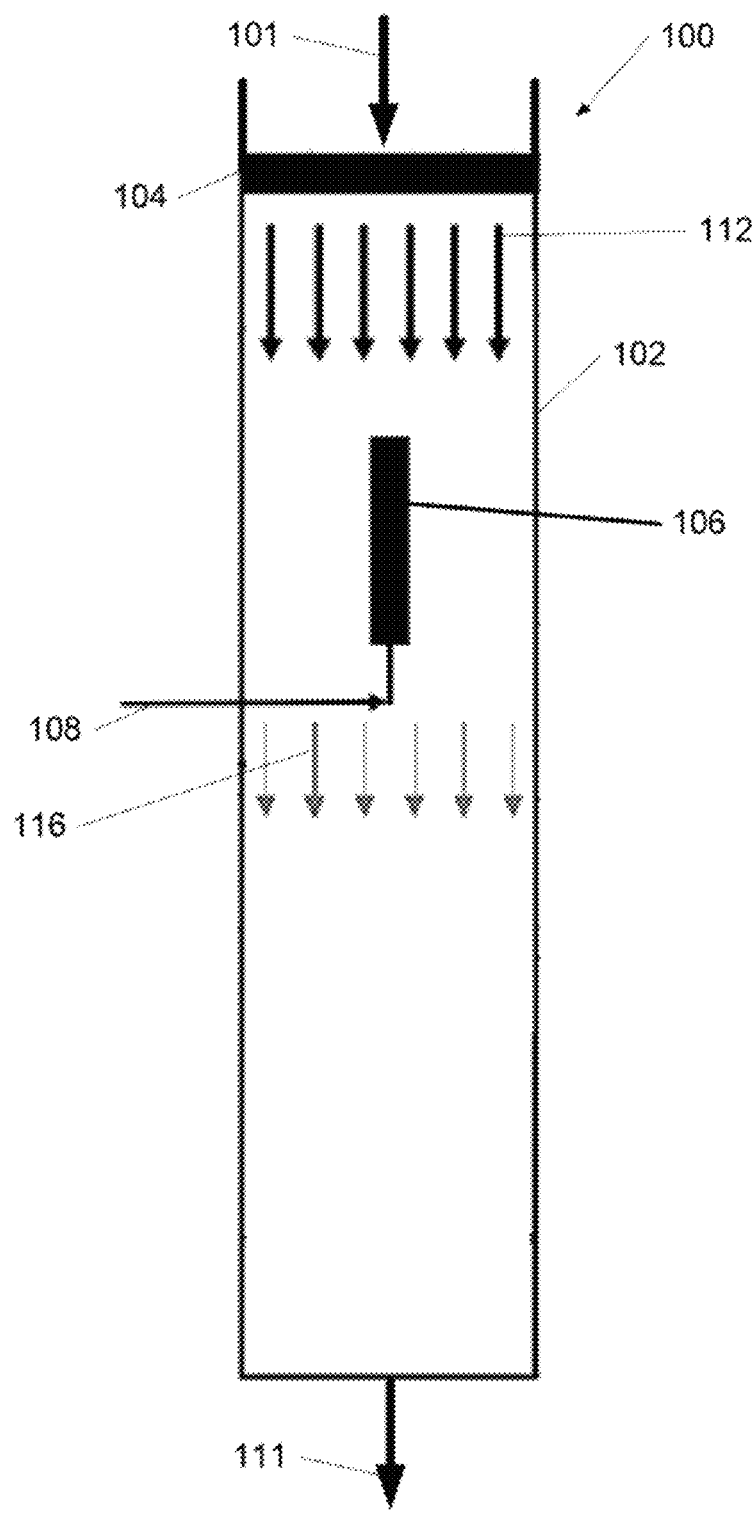
FIG. 1 schematically depicts a system for generating bubbles within a vessel, according to the systems and methods disclosed herein.

In the following description of the various embodiments, reference is made to the accompanying drawings, which form a part hereof, and in which is shown by way of illustration, ways various embodiments described herein may be practiced. It is to be understood that other embodiments may be utilized, and structural and functional modifications may be made without departing from the scope of the described embodiments. Embodiments described herein are capable of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged" and similar terms, is meant to include both direct and indirect mounting, connecting, coupling, positioning and engaging.

A "sparger" may comprise a device to introduce gas into a liquid, injected as bubbles, to agitate it or to dissolve the gas in the liquid. Example spargers may include orifice spargers, sintered spargers, and drilled pipe spargers. In certain configurations drilled pipe spargers may be mounted horizontally. In other examples, spargers may be mounted vertically or horizontally. In some examples, the sparger may be a perforated plate or ring, sintered glass, sintered steel, porous rubber pipe, porous metal pipe, porous ceramic or stainless steel, drilled pipe, stainless steel drilled pipe, polymeric drilled pipe, etc. The sparger may be of various grades (porosities) or may include certain sized orifices to produce a specific sized bubble or range of bubble sizes.

A "vessel", "reaction vessel", or "column" may be a vessel or container in which one or more gas and liquid streams, or flows may be introduced for bubble generation and/or fine bubble generation, and for subsequent gas-liquid contacting, gas-absorption, biological or chemical reaction, or surface-active material adsorption. In a reaction vessel, the gas and liquid phases may flow in the vertical directions. In a reaction vessel, larger bubbles from a sparger, having a buoyancy force larger than the drag force imparted by the liquid, may rise upwards. Smaller fine bubbles, having a buoyancy force less than or equal to the drag force imparted by the liquid, may flow downward with the liquid, as described by the systems and methods disclosed herein. A column or reaction vessel may not be restricted to any specific aspect (height to diameter) ratio. A column or reaction vessel may also not be restricted to any specific material and can be constructed from any material suitable to the process such as stainless steel, PVC, carbon steel, or polymeric material. A column or reaction vessel may contain internal components such as one or more static mixers that are common in biological and chemical engineering processing. A reaction vessel may also consist of external or internal heating or cooling elements such as water jackets, heat exchangers, or cooling coils. The reaction vessel may also be in fluid contact with one or more pumps to circulate liquid, bubbles, fine bubbles, and or one or more fluids of the system.

A "perforated plate" or "plate" may comprise a plate or similar arrangement designed to facilitate the introduction of liquid or additional liquid into the vessel that may be in the form of multiple liquid jets (i.e., accelerated liquid flow). The perforated plate may have a plurality of pores or orifices evenly or unevenly distributed across the plate that allow the flow of liquid from a top of the plate to the bottom of the plate. In some examples, the orifices may be spherical-shaped, rectangular-shaped, hexagonal prism-shaped, conical-shaped, pentagonal prism-shaped, cylindrical-shaped, frustoconical-shaped, or round-shaped. In other examples, the plate may comprise one or more nozzles adapted to generate liquid jets which flow into the column. The plate may also contain channels in any distribution or alignment where such channels are adapted to receive liquid and facilitate flow through into the reaction vessel. The plate may be made of stainless steel with a predefined number of laser-burnt, machined, or drilled pores or orifices. The specific orifice size may depend upon the required fine bubble size and required liquid, fine bubble, and/or fluid velocities. A specific orifice shape may be required to achieve the proper liquid acceleration and velocity from the plate to break or shear the sparger bubbles into the desired fine bubble size, and to create enough overall fluid downflow to carry the fine bubbles and liquid downward in the reaction vessel. The shape of the orifice may also impact ease of manufacturing and related costs. According to one embodiment, a straight orifice may be optimal due to ease of manufacture.

The term "fermentation" or "gas fermentation" and the like may be interpreted as the process which receives one or more substrate, such as syngas produced by gasification and produces one or more product through the utilization of one or more C1-fixing microorganisms. A "C1-fixing microorganism" may be a microorganism that has the ability to produce one or more products from a C1-carbon source. Typically, microorganisms disclosed herein may be a C1-fixing bacterium "C1" may refer to a one-carbon molecule, for example, CO, $CO_2$, $CH_4$, or $CH_3OH$. "C1-oxygenate" may refer to a one-carbon molecule that also comprises at least one oxygen atom, for example, CO, $CO_2$, or $CH_3OH$. "C1-carbon source" may refer to a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. In some examples, the C1-carbon source may comprise one or both of CO and $CO_2$. The fermentation process may include the use of one or more bioreactors. The phrases "fermenting," "fermentation process" or "fermentation reaction" and the like, as used herein, are intended to encompass both the growth phase and product biosynthesis phase of the gaseous substrate. Examples of C1-fixing microorganisms may include *Moorella, Clostridium, Ruminococcus, Acetobacterium, Eubacterium, Butyribacterium, Oxobacter, Methanosarcina, Desulfotomaculum, Clostridium autoethanogenum*, and combinations thereof.

The term "bioreactor" or "reactor" or "reactor vessel" and the like may include a device capable of being used for a fermentation process or a chemical conversion process. A bioreactor may consist of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor may be adapted to receive a gaseous substrate comprising $CH_4$, CO, $CO_2$ and $H_2$, and mixtures thereof. A fermentation process may comprise multiple reactors (stages), either in parallel or in series. For example, the fermentation process may comprise a first growth reactor in which the bacteria are cultured and a second fermentation reactor, to which fermentation broth from the growth reactor may be fed and in which most of the fermentation products may be produced.

A "fluid" as disclosed herein may include liquid, bubbles, and/or fine bubbles. The term "fermentation broth" or "broth" or "liquid" or "liquid growth medium" may encompass the mixture of components including nutrient media and a culture including one or more microorganisms. The fermentation process may utilize fermentation broth to ferment the gas bubbles or fine bubbles to one or more products. The bacterial culture may be maintained in an aqueous culture medium that contains nutrients, vitamins, and/or minerals sufficient to permit growth of the microorganism. The aqueous culture medium may be an anaerobic microbial growth medium, such as a minimal anaerobic microbial growth medium. "Nutrient media" or "nutrient medium" or "growth media" may also be used to describe the bacterial growth media. The fermentation process may utilize nutrient medium within the bioreactor. Generally, this term may refer to a media containing nutrients and other components appropriate for the growth of a microbial culture. The term "nutrient" may include any substance that may be utilized in a metabolic pathway of a microorganism. In some examples, nutrients may include potassium, vitamins, trace metals, and amino acids.

A "microorganism" is a microscopic organism, such as a bacterium, archaea, virus, or fungus. As used herein, recitation of "microbe" or "microorganism" or "culture" may encompass "bacterium." The terms microorganism, culture, and bacteria may be used interchangeably.

"Substrate" or "gas substrate" may refer to a carbon and/or energy source for the microorganism as disclosed herein. The substrate may be gaseous and may comprises a C1-carbon source, for example, CO, $CO_2$, and/or $CH_4$. In other examples, the substrate may comprise a C1-carbon source of CO, or CO and $CO_2$. In some examples, the substrate may be an industrial off gas or waste gas, such as CO or $CO_2$ or a mixture of both, produced by an industrial process such as ferrous metal products manufacturing, nonferrous products manufacturing, petroleum refining processes, gasification of coal, gasification of biomass, electric power production, carbon black production, and coke manufacturing. In yet other examples, the substrate may further comprise other non-carbon components, such as $H_2$ or $N_2$. The substrate may be sparged into the liquid media as bubbles. The bubbles may subsequently be converted to fine bubbles. The term fine bubble may also refer to a bubble that has been reduced in size. Fine bubbles generally include diameters in the range of about 0.1 mm to about 5 mm, or from about 0.5 mm to about 2 mm. In some examples, the fine bubbles disclosed herein may include a diameter from about 0.2 mm to about 1.5 mm. Fine bubbles may be spherical.

The microorganisms disclosed herein may be cultured with substrate fine bubbles to generate one or more products. For example, the microorganisms disclosed herein may generate ethanol, acetate, 1-butanol, butyrate, 2,3-butanediol, lactate, butene, butadiene, methyl ethyl ketone, ethylene, acetone, isopropanol, lipids, 3-hydroxypropionate, terpenes, including isoprene, fatty acids, 2-butanol, 1,2-propanediol, 1-propanol, 1-hexanol, 1-octanol, chorismate-derived products, 3-hydroxybutyrate, 1,3 butanediol, 2-hydroxyisobutyrate or 2-hydroxyisobutyric acid, isobutylene, adipic acid, 1,3 hexanediol, 3-methyl-2-butanol, 2-buten-1-ol, isovalerate, isoamyl alcohol, and monoethylene glycol. In certain examples, microbial biomass itself may be considered a product. One or more of these products may be further converted to produce at least one component of diesel, jet fuel, and/or gasoline. Additionally, the microbial biomass may be further processed to produce at least a portion of a single cell protein. A "single cell protein" may refer to a microbial biomass that may be used in protein-rich human and/or animal feeds, often replacing conventional sources of protein supplementation such as soymeal or fishmeal. The ethanol generated may be further converted to ethylene which may be used on its own or may be used as a raw material for additional chemical products such as polyethylene (PE), polyethylene terephthalate (PET) and polyvinyl chloride (PVC) as well as fibers and other organic chemicals, or chlorinated to ethylene dichloride and then cracked to vinyl chloride monomer. Other ethylene derivatives include alpha olefins used in liner low-density polyethylene production detergent alcohols and plasticizer alcohols, and vinyl acetate monomers. Ethylene oxides produced may be converted to monoethylene glycol which in turn may be converted to polyester resin polyethylene terephthalate (PET). Isopropanol may be converted to polypropylene.

The systems and methods as disclosed herein, employ, within a vessel, multiple liquid jets or portions of accelerated liquid flow generated using the perforated plate to accelerate liquid and break bubbles into smaller fine bubbles having a greater superficial surface area than the original bubbles. The original bubbles are initially generated by injecting gas with a sparger positioned entirely within the reaction vessel. In one example, original bubbles injected into liquid from a sparger may have a diameter of about 2 mm to about 20 mm. In another example, original bubbles injected into liquid from a sparger may have a diameter of about 5 mm to about 15 mm. In other examples, original bubbles injected into liquid from a sparger may have a diameter of about 7 mm to about 13 mm. Upon injection, the original bubbles subsequently migrate upwards through the liquid and encounter the multiple liquid jets or portions of accelerated liquid flow which breaks the original bubbles into fine bubbles. The resulting fine bubbles and liquid flow down the reactor vessel in the downward fluid flow. The fine bubbles of substrate provide a carbon source and optionally an energy source to the microbes which then produce one or more desired products. The spargers are positioned within the vessel to create a first zone for the original bubbles to rise within the vessel, and to create a second zone for the accelerated liquid to break the original bubbles into fine bubbles and for fluid to flow through the vessel, where the fluid comprises the accelerated portion of the liquid and fine bubbles.

Due to the nature of the multi-phase system, one approach to maximizing product generation is to increase gas to liquid mass transfer. The more gas substrate transferred to a reaction liquid, the greater the desired product generated. The smaller fine bubbles of the present disclosure provide an increased superficial surface area resulting in an increased gas to liquid mass transfer rates overcoming known solubility issues. Additionally, the downflow reactor systems disclosed herein are effective to increase the residence time of the fine bubbles. The increased time that the fine bubbles remain in the reaction liquid generally provides increased amounts of reaction product generated, as well as greater surface areas in contact with the microbes. As such, the systems and methods disclosed herein improve over previous systems by generating fine bubbles that maximize gas to liquid superficial surface areas leading to high gas to liquid mass transfer rates. Further, the systems and methods disclosed herein provide superficial gas and liquid velocities not achieved by the previous systems and methods resulting in the generation of fine bubbles with high gas phase residence time resulting in the efficient creation of chemical and biological reaction products.

FIG. 1 illustrates an example of a system of generating bubbles in a vessel 100. System 100 comprises cylindrical reactor 102. Liquid enters inlet or top portion 101 of reactor 102. The liquid may enter top portion 101 via an external pump in fluid communication with system 100. According to certain embodiments, the liquid entering top portion 101 is recirculated by an external pump in fluid communication with system 100. The liquid enters the top of perforated plate 104 and the liquid is accelerated by passing though the orifices in plate 104. According to certain examples, plate 104 may be configured to accelerate, for example, at least, greater than, less than, equal to, or any number from about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99 to about 100% of the liquid in reactor 102. Sparger 106 injects gas bubbles into the liquid from gas source 108. Sparger 106 is positioned within reactor 102 such that a first zone is created in which the injected bubbles rise within reactor 102 and encounter accelerated liquid 112 exiting the bottom of plate 104. Accelerated liquid 112 from plate 104 breaks the rising bubbles into fine bubbles thereby increasing the superficial surface area required for the desired chemical or biological reaction. The fine bubbles may have a diameter in the range of about 0.1 mm to about 5 mm, or from about 0.5 mm to about 2 mm. In some examples, the fine bubbles may include a diameter from about 0.2 mm to 1.5 mm. According to another embodiment, the diameter of the fine bubbles may be, for example, at least, greater than, less than, equal to, or any number in between about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5.0 mm. Sparger 106 is further positioned within reactor 102 such that a second zone is created in which the fluid flow of liquid and fine bubbles may flow downward.

The fine bubbles may have a decreased rise velocity compared to the injected bubbles. Due to the overall flow of the accelerated liquid, fluid 116, containing the liquid and the fine bubbles, may have a net downward flow. The downward velocity of fluid 116 is greater than the overall rise velocity of the fine bubbles. Fluid 116 may exit reactor 102 at outlet 111. Plate 104 may have a thickness (and a depth of the orifices) from about 1 mm to 25 mm. According to another embodiment, the thickness of the plate may be, for example, at least, greater than, less than, equal to, or any number in between about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm.

The dimensions of the components of system 100, as illustrated in FIG. 1, may vary depending upon the required use or process. According to certain embodiments, the diameter of the reactor 102 may be, for example, at least, greater than, less than, equal to, or any number in between about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 to about 20.0 meters. According to other embodiments, the length of the reactor 102 may be, for example, at least, greater than, less than, equal to, or any number in between about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.5, 21.5, 22.0, 22.5, 23.0, 23.5, 24.0, 24.5, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0 to about 50.0 meters.

The velocity of the liquid or a portion of the liquid accelerated from plate 104 can be determined by the following equation:

$$Q_L = N \times (\pi/4) \times d^2 \times V_j$$

where $Q_L$ is the liquid volumetric flow rate (m³/s), $v_j$ is the jet velocity, N is the total number of orifices on the plate, d is the diameter of the orifices, and π is the mathematical symbol pi. According to one embodiment, the velocity of the accelerated liquid from plate 104 may be, for example, at least, greater than, less than, equal to, or any number in between about 5000, 5500, 6000, 6500, 7000, 7500, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500 to about 20000 mm/s. As depicted in FIG. 1, the velocity of accelerated liquid 112 is critical to breaking bubbles injected into the liquid by sparger 106 into properly sized fine bubbles, and to ensuring that the fluid of liquid and fine bubbles has enough velocity to generate a net downward fluid flow. The superficial liquid velocity, $V_L$, in the main reaction vessel may be calculated by the following equation: $V_L = Q_L/A_C$ where $Q_L$ is the volumetric flow rate of the liquid (m³/s) in the reaction vessel and $A_C$ is the cross-sectional area of the reaction vessel. Therefore, superficial liquid velocity represents velocity of the liquid phase if it occupied the entire cross-sectional area of the reaction vessel. According to embodiments, the superficial liquid velocity may also include zones or voids of stagnant liquid and fine bubbles, and/or net downward fluid flow. For the same liquid flow rate, the gas flow rate can vary depending on the actual application. Superficial velocity of the gas phase $V_G$ may be determined by the following equation: $V_G = Q_G/A_C$ where $Q_G$ is the volumetric flow rate of the gas (m³/s) injected into the liquid from the sparger(s) and $A_C$ is the cross-sectional area of the reaction vessel. According to another embodiment, the superficial velocity of the gas phase in the vessel may be, for example, at least, greater than, less than, equal to, or any number in between about 5, 10, 15, 20, 25, 30, 35, 40, 45, 50, 55, 60, 65, 70, 75, 80, 85, 90, 95 to about 100 mm/s. According to still another embodiment, the superficial velocity of the gas phase in the vessel may be, for example, approximately 50-60 mm/s.

Positioning of a sparger or multiple spargers 106 within reactor 102, and in an upper portion of reactor 102 has the additional advantage of decreasing hydrostatic pressure at the top of reactor 102 facilitating increased gas to liquid mass transfer rates with decreased energy requirements. Further, required reactor components are minimized, yet gas to liquid mass transfer rates are maximized with a smaller reactor footprint due to decreased reactor size. In some embodiments, for example, the systems and methods disclosed herein achieve gas to liquid mass transfer rates of at least 125 m³/min. In other examples, the gas to liquid mass transfer rates may be, for example, at least, greater than, less than, equal to, or any number in between about 100, 105, 110, 115, 120, 125, 130, 135, 140, 145, 150, 155, 160, 165, 170, 175, 180, 185, 190, 195 to about 200 m³/min. Additionally, the sparger configurations, superficial velocities of the gas and liquid phases achieved, and the increased gas to liquid mass transfer rates disclosed herein overcome known obstacles associated with the use of a gas and liquid phase system of the previous and conventional reactors. Particularly in bioreactors having a gas substrate and an aqueous culture.

Figure 2:
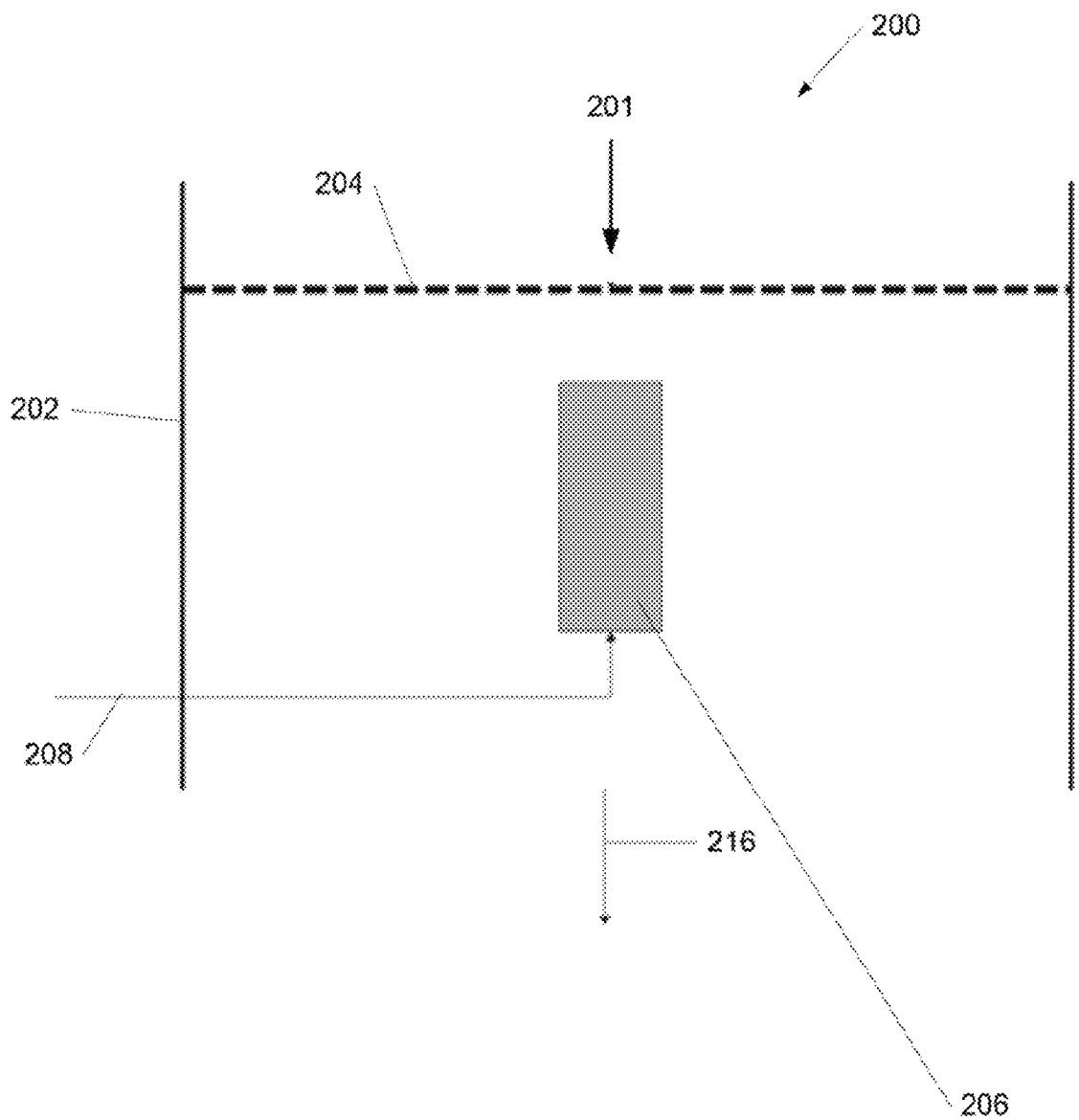
FIG. 2 illustrates a side, cross-sectional view of a gas sparger configured within a system for generating bubbles within a vessel, according to the systems and methods disclosed herein.

FIG. 2 illustrates a side, cross-sectional view of gas sparger 206 positioned within system of generating bubbles in a vessel 200. Sparger 206 may be positioned entirely within reactor 202 of system of generating bubbles in a vessel 200. Sparger 206 may be positioned in a vertical orientation. According to certain embodiments, sparger 206 may be positioned perpendicular to plate 204. According to other embodiments, sparger 206 may be positioned within at least +/−15 degrees of a pure vertical orientation. Alternatively, sparger 206 may be positioned generally horizontally. Sparger 206 may inject bubbles into the liquid. The bubbles injected into the liquid may be from about 2 mm to about 20 mm or from greater than about 5 to about 15 mm, or from about 7 to about 13 mm. According to one embodiment, the diameter of the bubbles injected into the liquid by the sparger may be, for example, at least, greater than, less than, equal to, or any number in between about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0 to about 20.0 mm. Liquid inlet 201 provides a conduit for liquid flow into the top of plate 204 and then through the orifices of plate 204 generating an accelerated fluid flow. Injected bubbles rise to the top portion of reactor 202 and the bubbles are broken into fine bubbles by the accelerated liquid flow from plate 204. Sparger 206 receives gas from gas source 208 for injecting bubbles into the liquid. Sparger 206 may be positioned entirely within the reactor 202 to maximize the amount of injected bubbles for the subsequent generation of fine bubbles. In some examples, the top of sparger 206 may be positioned at a distance from the bottom of the plate 204 to maximize fine bubble generation and consistent fluid flow to minimize or prevent stagnant zones or voids near the plate 204 and sparger 206. According to one embodiment, the top of the sparger 206 may be positioned, for example, at least, greater than, less than, equal to, or any number in between about 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 mm from the bottom of the plate 204. Again, due to the overall flow of the accelerated liquid, fluid 216, containing the liquid and the fine bubbles, may have a net downward flow. The downward velocity of fluid 216 is greater than the overall rise velocity of the fine bubbles.

Figure 3:
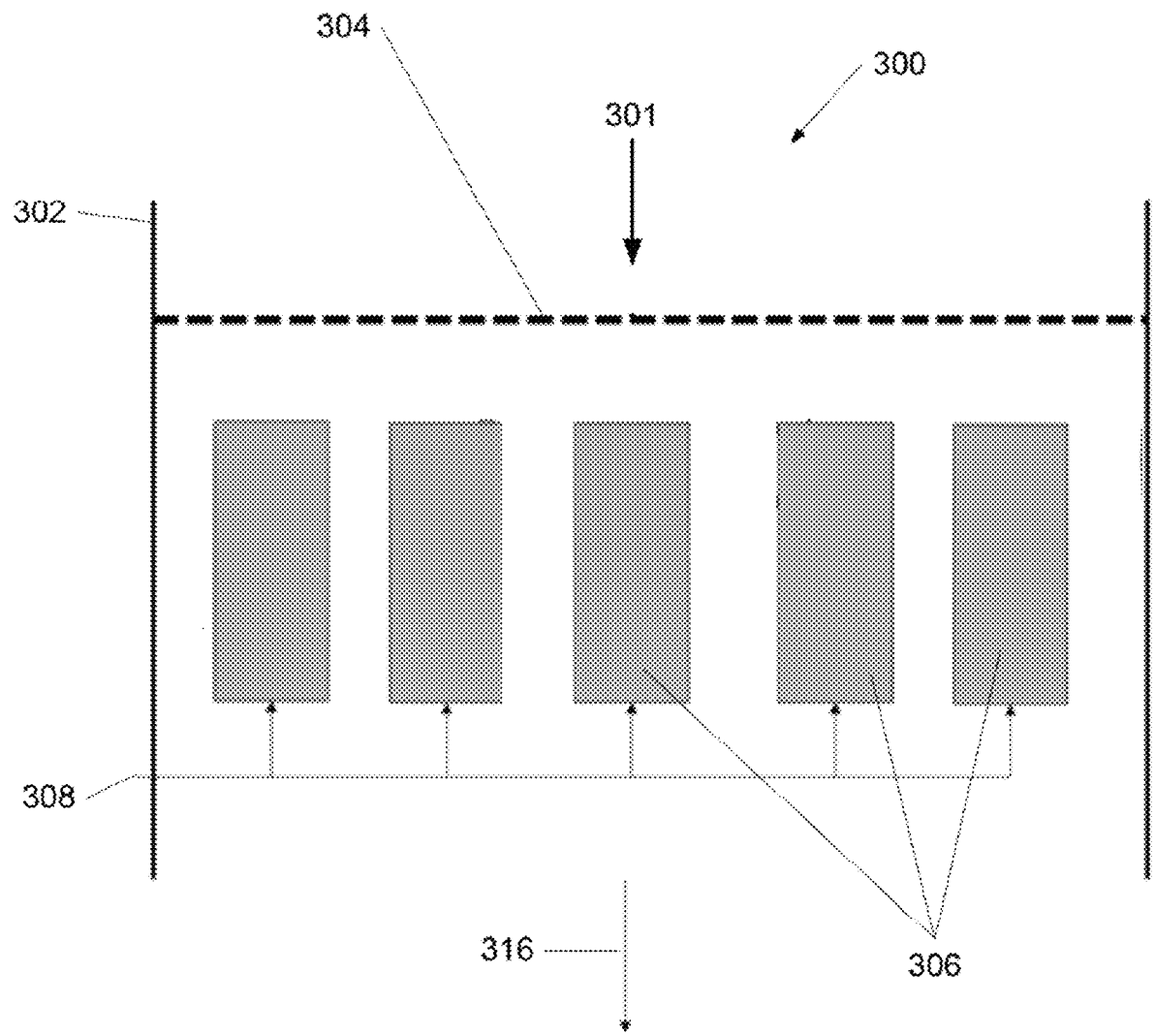
FIG. 3 illustrates a side, cross-sectional view of an alternative embodiment of gas sparger system configured within a system for generating bubbles within a vessel, according to the systems and methods disclosed herein.

FIG. 3 illustrates a side, cross-sectional view of an alternative embodiment of an example gas sparger system positioned entirely within reactor 300. Spargers 306 may be positioned entirely within reaction vessel 302. Spargers 306 may be positioned in a vertical orientation. Alternatively, spargers 306 may be positioned horizontally. Like sparger 206 of FIG. 2, spargers 306 inject bubbles into the reaction broth or liquid. Liquid inlet 301 provides a conduit for liquid flow onto the top of plate 304. The bubbles rise to the top portion of reaction vessel 302 and the bubbles are broken into fine bubbles in turbulent zone created by accelerated liquid flow from plate 304. Spargers 306 receive a gas source 308 for injecting bubbles into the liquid. Again, spargers 306 may be positioned entirely within reaction vessel 302 to maximize the generation of bubbles and then fine bubbles. Positioning of spargers 306 may also maximize consistent and efficient fluid flow to prevent zones of stagnant fluid. In some examples, the top of spargers 306 may be positioned at a distance from the bottom of plate 304 to maximize fine bubble generation as previously described with FIG. 2. According to another embodiment, gas flow from gas supply 308 to spargers 306 may be regulated by a sparger manifold(s) (not shown) to allow efficient start up conditions and to maintain a constant fluid flow rate. Additionally, the ability to control gas flow from gas supply 308 to sparger 306 may be critical to biological reactions. Fluid 316, containing the liquid and the fine bubbles, may have a net downward velocity that may be greater than the overall rise velocity of the fine bubbles. Multiphase flow containing liquid and fine bubbles continues with an overall downflow shown as 316 in reaction vessel 302.

Figure 4:
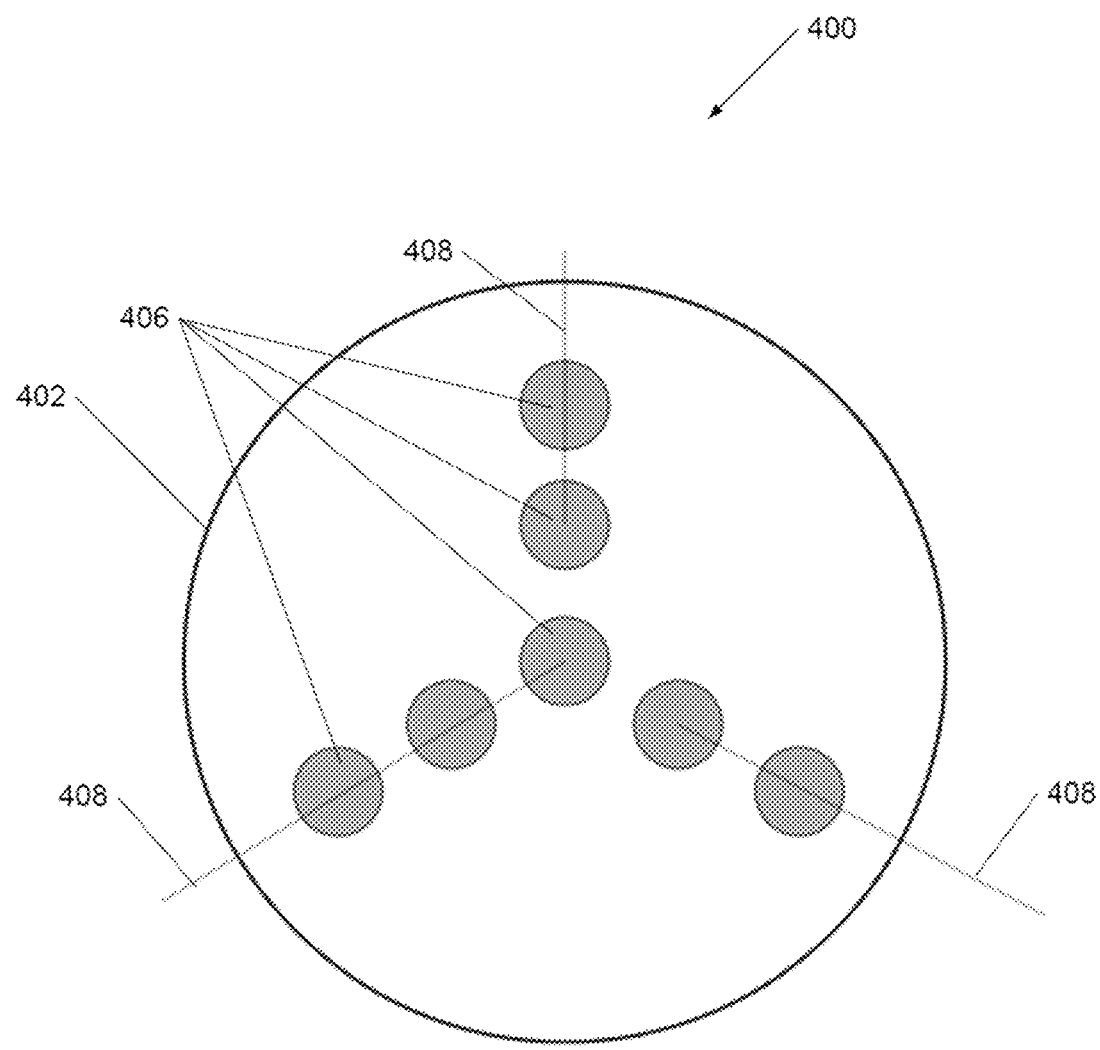
FIG. 4 illustrates a top, cross-sectional view of a sparger system, according to the systems and methods disclosed herein.

FIG. 4 illustrates an alternative top, cross-sectional view of the sparger system of FIG. 3. The configuration of spargers 406 may include the depicted 3-arm configuration. According to other embodiments, 4-arm, 6-arm, 8-arm, and 10-arm configurations are also contemplated. According to another embodiment, the system may employ a single center sparger 406 configuration or a spider configuration with multiple spargers 406. According to another embodiment, the system may employ a spoke and hub configuration, or an antler configuration, both with multiple spargers 406 positioned in a symmetrical pattern or with multiple spargers 406 positioned in random/nonsymmetrical configurations. According to one embodiment, spargers 406 may be in a configuration to facilitate the generation of specific zones that allow injected bubbles to rise within the liquid or fluid. The spargers 406 may be fluidly engaged with gas supplies 408. According to another embodiment, gas flow from gas supply 408 to an individual sparger 406 or a group of spargers 406 may be regulated by one or more sparger manifolds (not shown) to allow efficient start up conditions and or to maintain a constant fluid down flow rate, and to minimize system disruption for maintenance requirements/ repairs or cleaning. Plurality of spargers 406 may be positioned entirely within vessel 402 of reactor system 400. Spargers 406 may also be positioned vertically within vessel 402. Multiple spargers 406 may positioned within an upper portion of vessel 402 for the efficient generation of fine bubbles. According to other embodiments, spargers 406 may be positioned in a bottom portion of vessel 402 or in a middle portion of vessel 406. According to another embodiment, spargers 406 may be oriented in a horizontal position. Again, positioning and configuration of spargers 406 may also maximize consistent fluid flow within vessel 402 preventing zones of stagnant fluid. According to yet another embodiment, spargers 406 and gas supply 408 may be configured as modular components facilitating the ease of reactor construction and/or component replacement, general maintenance, cleaning, and for allowing for a scalable reactor system depending upon the requirements. In accordance with other embodiments, multiple levels or stacks of spargers 406 and respective gas supplies 408 may be configured within vessel 402.

Figure 5:
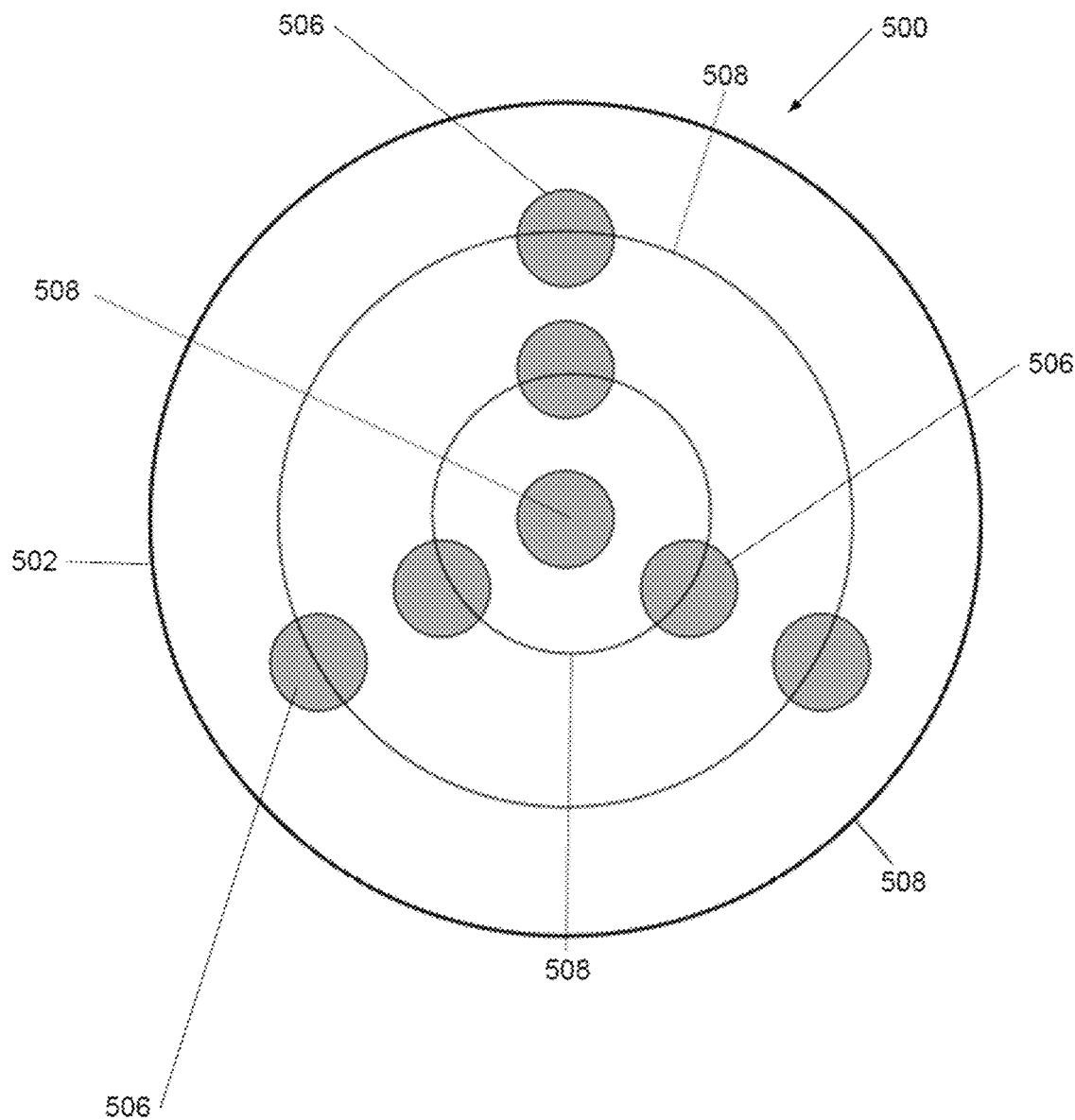
FIG. 5 illustrates a top, cross-sectional view of an alternative embodiment of a sparger system, according to the systems and methods disclosed herein.

FIG. 5 illustrates an alternative embodiment of an example sparger system of a fine bubble reactor 500. Spargers 506 may be positioned entirely within vessel 502. Spargers 506 may be fluidly engaged to an annular gas supply 508. According to other embodiments, spargers 506 may be positioned in a bottom portion of vessel 502 or in a middle portion of vessel 506. According to another embodiment, spargers 506 may be oriented in a horizontal position. According to still another embodiment, spargers 506 may be positioned in multiple positions throughout vessel 502 to include the upper, middle, and lower portions of the vessel 502. According to yet another embodiment, spargers 506 may be a ring sparger or a drilled-pipe sparger. According to one embodiment, individual spargers 506 and annular gas supply 508 may be configured as modular components facilitating the ease of reactor construction and/or component replacement, general maintenance, cleaning, or allowing for a scalable reactor system depending upon the requirements. In accordance with other embodiments, multiple levels of spargers 506 and annular gas supplies 508 may be stacked within vessel 502. In still other embodiments, spargers 506 may be configured to extend vertically below the annular gas supply 508, or spargers 506 may be configured to extend vertically above the annular gas supply 508. According to another embodiment, a single level or stack of annular gas supplies 508 may include, for example, at least, greater than, less than, equal to, or any number in between about 1, 2, 3, 4, 5, 6, 7, 8, 9, 10, 11, 12, 13, 14, 15, 16, 17, 18, 19 to about 20 individual annular gas supplies 508.

Figure 6A:
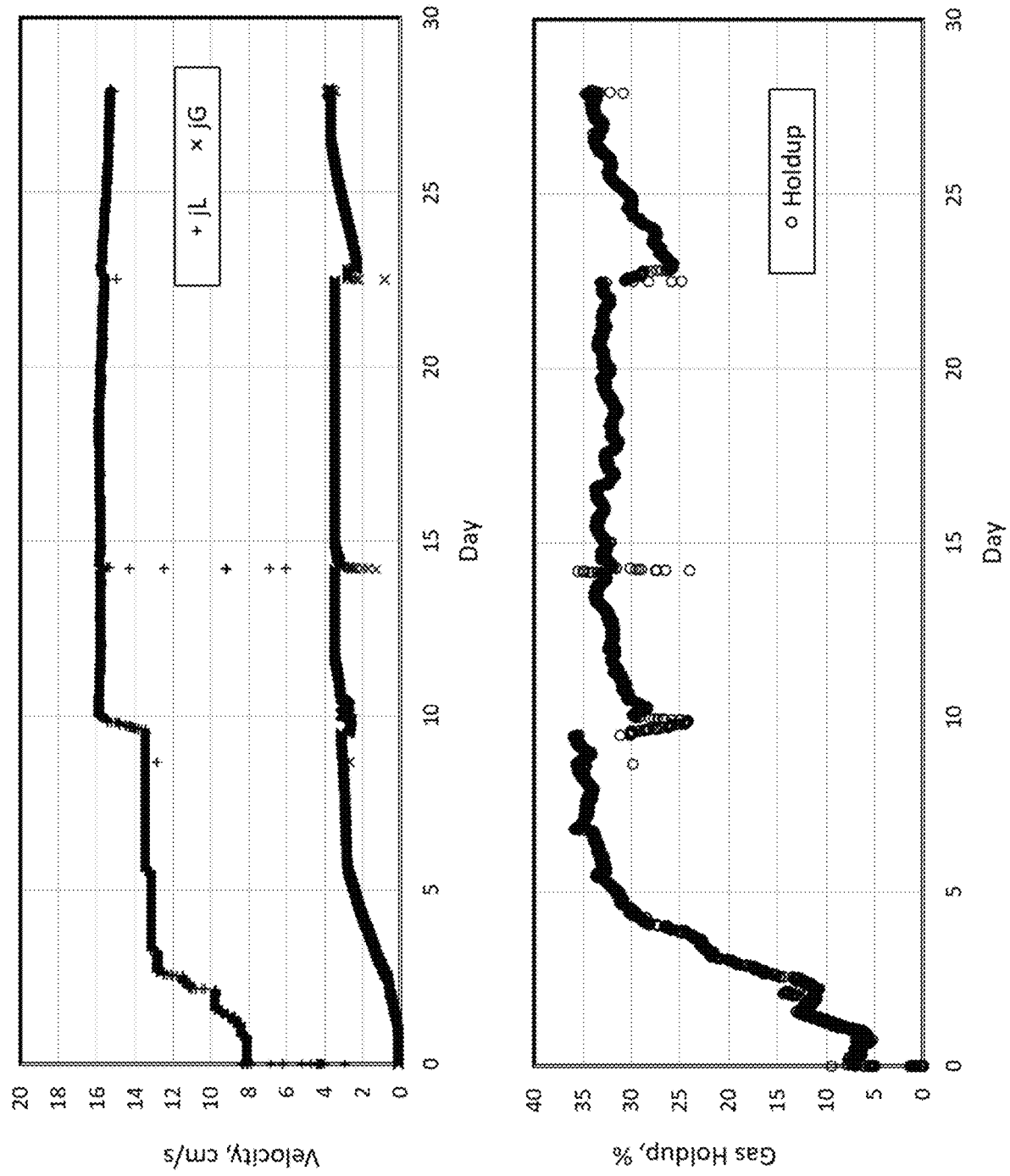
FIG. 6a and FIG. 6b graphically depict typical superficial liquid and gas velocities, and gas holdup generated by two systems for generating bubbles within a vessel. The systems and methods disclosed herein generated superficial velocities of the gas phase that exceeded 35 mm/s.
Figure 6B:
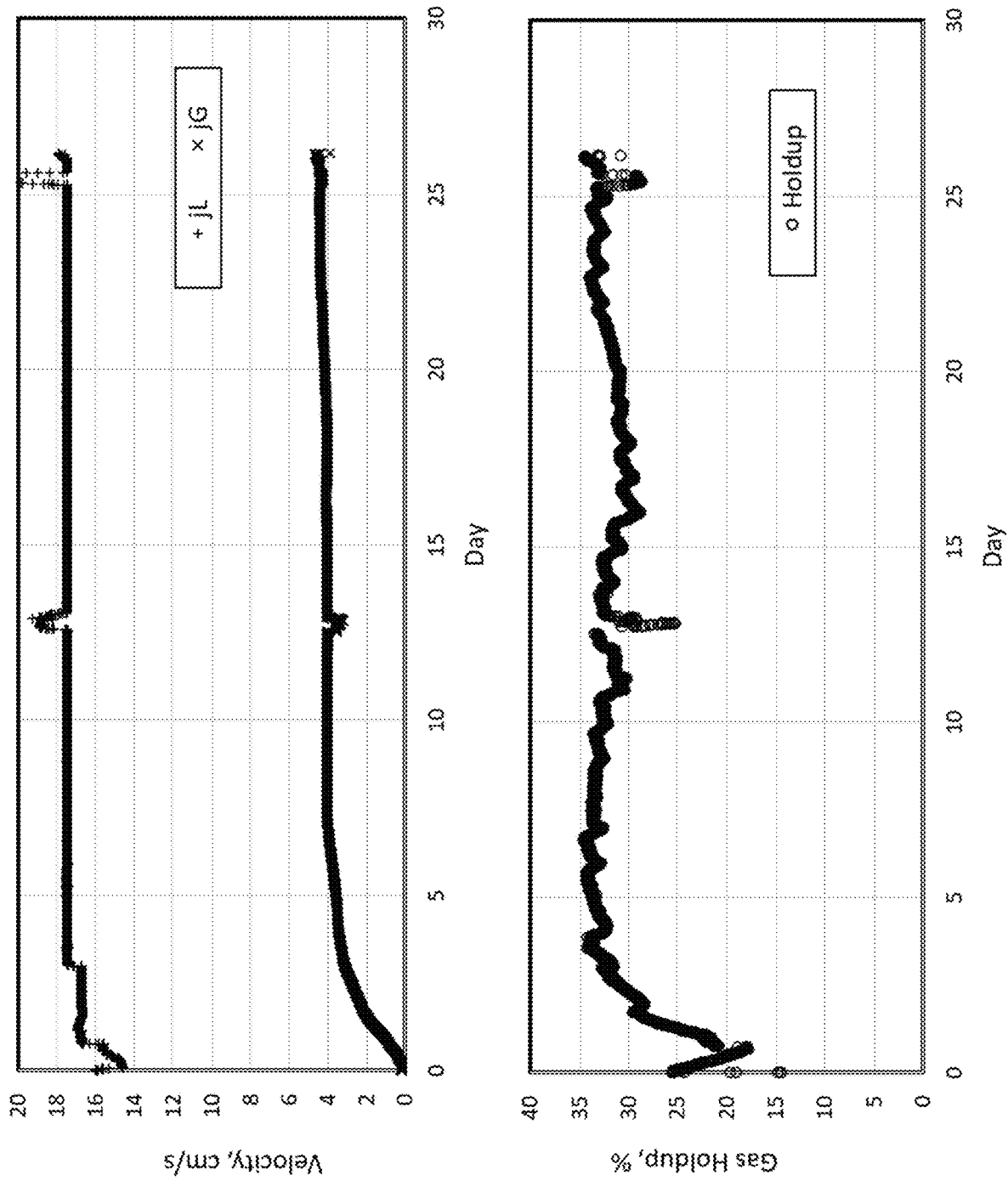

FIGS. 6a and 6b graphically depicts typical superficial liquid and gas velocities, and gas holdup generated by the example fine bubble reactors and related methods disclosed herein. The top graph in each of FIG. 6a and FIG. 6b plots liquid superficial velocities (jL) annotated with a "+" symbol. Gas superficial velocities (jG) are also plotted on the top graph in each of FIG. 6a and FIG. 6b and annotated with an "x" symbol. The bottom graph in each of 6a and 6b plots gas holdup annotated with an "o" symbol. The plots depict the superficial liquid and gas velocities, and gas holdup generated by the test apparatus over a 27-day experimental run, as depicted on the X axis. Velocities and holdup percentages are depicted on the Y axis. Typical superficial velocities achieved by example systems include average gas superficial velocities (jG) of about 3.5 cm/s (FIG. 6a) and about 4.2 cm/s (FIG. 6b) and liquid superficial velocities (jL) of about 15.9 cm/s (FIG. 6a) and about 17.5 cm/s (FIG. 6b) with an average gas holdup of about 32.0% (FIGS. 6a and 6b). Notably, the gas holdup and reactor liquid level remained fairly constant during the 27-day trial period of continuous operation of the reactor. In general, the example reactor performance shown in FIG. 6a and FIG. 6b included even distribution and increased density of fine bubbles and ease of maintenance as a result of the simplified designs disclosed herein.

Figure 7:
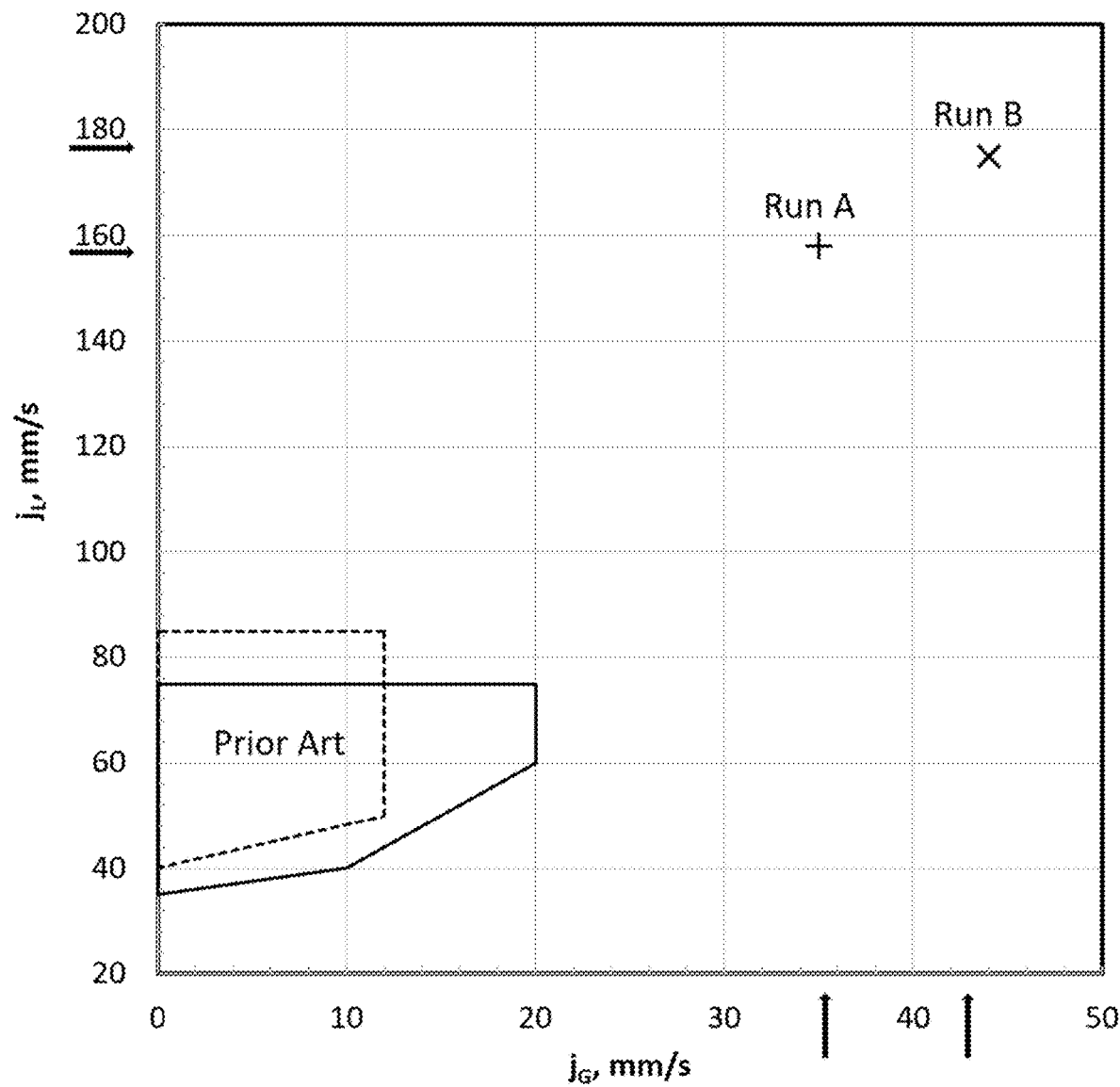
FIG. 7 graphically depicts typical superficial liquid and gas velocities generated by previous systems in comparison with superficial velocities of the gas phase generated by the present disclosure. Superficial velocities of the gas phase as shown in FIGS. 6a and 6b are plotted in comparison to prior art.

In contrast to the systems and methods disclosed herein, FIG. 7 graphically depicts typical superficial liquid and gas velocities of prior art reactor systems. Prior art systems could not exceed generation of superficial gas velocities ($V_G$) of about 25 mm/s as shown, for example, in FIG. 1(C) of Kalaga, Dinesh V., et al. "Scale-up of a downflow bubble column: Experimental investigations." *Chemical Engineering Journal* (2020). In comparison, the "+" depicted at about 35 mm/s depicts the superficial gas velocities generated by the example described in FIG. 6a, the "x" depicted at about 42 mm/s depicts the superficial gas velocities generated by the example described in FIG. 6b, which clearly exceeds the maximum performance of the prior art and conventional systems. The additional arrow shown at 158 mm/s of the Y-axis notes the superficial liquid velocities generated by the example described in FIG. 6a, again clearly exceeding the maximum performance of the prior art and conventional systems. Finally, the arrow shown at 178 mm/s of the y-axis notes the superficial liquid velocities generated by the example described in FIG. 6b, yet again clearly exceeding the maximum performance of the prior art and conventional systems.

The systems and methods disclosed herein may be configured as a bioreactor for the conversion of gaseous substrate, such as waste substrates, into useful products via microbial fermentation. For example, substrate bubbles of at least one C1 carbon source may be sparged into the reaction vessel containing a liquid growth medium. The perforated plate may be configured to accelerate at least a portion of the liquid growth medium in the vessel. The liquid growth medium accelerated from the plate may be used to break the substrate bubbles into substrate fine bubbles to maximize gas to liquid mass transfer of the C1 carbon source and increase the amount of substrate available to the microbes. The system may generate a superficial velocity of the gas phase in the vessel of at least 30 mm/s. The microorganism culture in the liquid growth medium may anaerobically ferment the substrate to produce at least one fermentation product and with the higher superficial velocity of the gas phase in the vessel the productivity of the system is increased.

Although the present disclosure has been described in certain specific embodiments, many additional modifications and variations would be apparent to those skilled in the art. It is therefore to be understood that the present disclosure may be practiced otherwise than specifically described without departing from the scope and spirit of the present disclosure. Thus, embodiments of the present disclosure should be considered in all respects as illustrative and not restrictive. Accordingly, the scope of the disclosure should be determined not by the embodiments illustrated, but by the appended claims and their equivalents.

The invention claimed is:

1. An apparatus for generating fine bubbles comprising:
a vessel containing a liquid and having a liquid inlet;
a plate comprising a plurality of orifices positioned in an upper portion of the vessel and below the liquid inlet wherein the orifices are sized to accelerate at least a portion of the liquid in the vessel;
at least two gas supplies each gas supply comprising three or more spargers positioned within the vessel with a surface of the spargers positioned from about 50 mm to about 1000 mm from a bottom of the plate and the spargers sized to inject from about 7 mm to about 13 mm diameter bubbles into the liquid;
the spargers positioned within the vessel to create a first zone for the bubbles to rise within the vessel, and to create a second zone for the accelerated liquid to break the bubbles into fine bubbles and for fluid having the accelerated portion of the liquid and fine bubbles to flow through the vessel.

2. The apparatus of claim 1, wherein the spargers are sintered spargers or orifice spargers.

3. The apparatus of claim 1, wherein a thickness of the plate is about 1 mm to about 25 mm.

4. The apparatus of claim 1, wherein the spargers are positioned perpendicular to the plate.

5. The apparatus of claim 1, wherein the plate comprising the plurality of orifices is sized to accelerate at least 90% of the liquid in the vessel.

6. A bioreactor apparatus comprising:

a vessel having a liquid inlet;

a plate comprising a plurality of orifices positioned in an upper portion of the vessel and below the liquid inlet, wherein the orifices are sized to accelerate at least a portion of a liquid contained in the vessel;

at least one gas source connected to at least one sparger manifold;

at least two gas supplies each gas supply comprising three or more spargers positioned within the vessel with a surface of the spargers positioned from about 50 mm to about 1000 mm from a bottom of the plate and the spargers sized to inject from about 7 mm to about 13 mm diameter gas bubbles into the liquid;

the spargers positioned within the vessel to create a first zone wherein bubbles to rise within the vessel, and to create a second zone wherein the accelerated liquid breaks the bubbles into fine bubbles;

wherein each gas supply is connected to a corresponding sparger manifold.

7. The apparatus of claim 1 wherein the gas supplies are in an arm configuration.

8. The apparatus of claim 1 wherein the gas supplies are annular.

9. The apparatus of claim 6, wherein the gas supplies are in an arm configuration.

10. The apparatus of claim 6, wherein the gas supplies are annular.

\* \* \* \* \*